(12) United States Patent
Peglion et al.

(10) Patent No.: US 8,476,426 B2
(45) Date of Patent: Jul. 2, 2013

(54) PROCESS FOR THE SYNTHESIS OF IVABRADINE AND ADDITION SALTS THEREOF WITH A PHARMACEUTICALLY ACCEPTABLE ACID

(75) Inventors: Jean-Louis Peglion, Le Vesinet (FR); Aimee Dessinges, Rueil Malmaison (FR)

(73) Assignee: Les Laboratoires Servier, Suresnes Cedex (FR)

( * ) Notice: Subject to any disclaimer, the term of this patent is extended or adjusted under 35 U.S.C. 154(b) by 27 days.

(21) Appl. No.: 13/369,690

(22) Filed: Feb. 9, 2012

(65) Prior Publication Data
US 2012/0208996 A1    Aug. 16, 2012

(30) Foreign Application Priority Data

Feb. 14, 2011    (FR) ...................... 11 00446

(51) Int. Cl.
C07D 223/16    (2006.01)
C07C 211/00    (2006.01)
C07C 223/00    (2006.01)

(52) U.S. Cl.
USPC ............ 540/523; 564/161; 564/306; 564/428

(58) Field of Classification Search
USPC ............................ 540/523; 564/161, 306, 428
See application file for complete search history.

(56) References Cited

U.S. PATENT DOCUMENTS

| 8,097,720 B2 | 1/2012 | Peglion et al. |
| 2010/0249398 A1 | 9/2010 | Peglion et al. |

FOREIGN PATENT DOCUMENTS

| EP | 2202225 | 6/2010 |
| EP | 2241553 | 10/2010 |
| WO | WO2005/110993 | 11/2005 |
| WO | WO2010/072409 | 7/2010 |

OTHER PUBLICATIONS

French Search Report for FR1100446 of May 16, 2011.

*Primary Examiner* — Bruck Kifle
(74) *Attorney, Agent, or Firm* — Hueschen and Sage

(57) ABSTRACT

Process for the synthesis of ivabradine of formula (I):

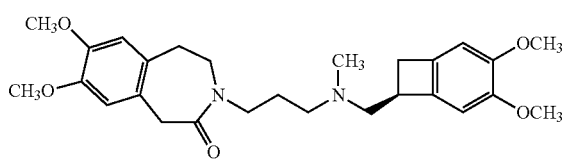

(I)

and addition salts thereof with a pharmaceutically acceptable acid.

19 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

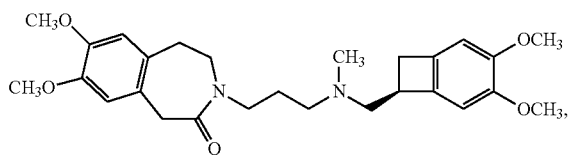
(I)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid, and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the synthesis of ivabradine hydrochloride starting from the compound of formula (II):

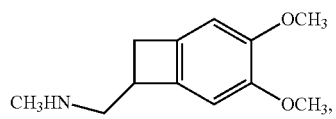
(II)

which is resolved to yield the compound of formula (III):

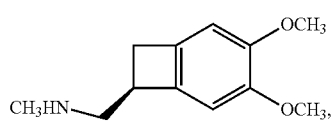
(III)

which is reacted with the compound of formula (IV):

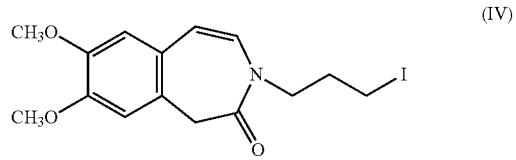
(IV)

to yield the compound of formula (V):

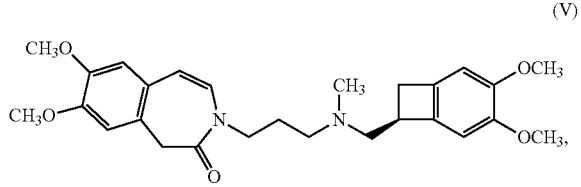
(V)

the catalytic hydrogenation of which yields ivabradine, which is then converted into its hydrochloride.

The disadvantage of that synthesis route is that it results in ivabradine in a yield of only 1%.

In view of the pharmaceutical value of this compound, it has been important to be able to obtain it by an effective synthesis process resulting in ivabradine in a good yield.

The present invention relates to a process for the synthesis of ivabradine of formula (I):

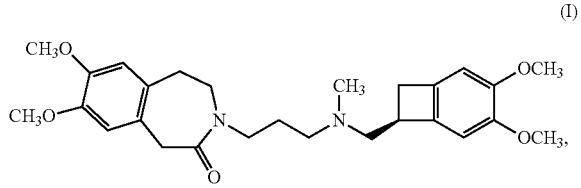
(I)

which process is characterised in that the compound of formula (VI):

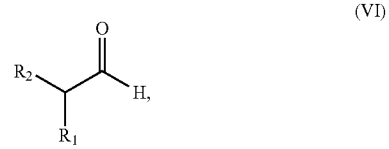
(VI)

wherein $R_1$ and $R_2$, which are the same or different, represent linear or branched ($C_1$-$C_6$)alkoxy groups or together with the carbon atom carrying them form a 1,3-dioxane, 1,3-dioxolane or 1,3-dioxepane ring, is subjected to a reductive amination reaction with the compound of formula (VII):

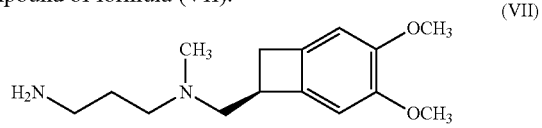
(VII)

in the presence of a reducing agent,
in an organic solvent, a mixture of organic solvents or a mixture of organic solvent(s) and water, to yield the compound of formula (VIII):

(VIII)

wherein $R_1$ and $R_2$ are as defined hereinbefore,
which is subjected to a condensation reaction with the compound of formula (IX):

(IX)

in the presence of a base in an organic solvent,
to yield the compound of formula (X):

(X)

wherein $R_1$ and $R_2$ are as defined hereinbefore,
which is subjected to a cyclisation reaction in an acid medium to yield the compound of formula (V):

(V)

which is subjected to a hydrogenation reaction to yield ivabradine of formula (I), which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

A list of reducing agents which may be used to carry out a reductive amination reaction is available in the reference works *Comprehensive Organic Transformations* (Richard C. Larock, VCH Publishers 1989, pp 421-425) and *Advanced Organic Chemistry Fourth Edition* (Jerry March, Wiley Interscience 1992, pp 898-900).

Among the reducing agents which may be used to carry out the reductive amination reaction of the compound of formula (VI) with the compound of formula (VII) there may be mentioned, without implying any limitation, sodium triacetoxyborohydride, sodium cyanoborohydride, and dihydrogen in the presence of a catalyst such as palladium, platinum, nickel, ruthenium, rhodium, and compounds thereof, especially on a support or in the form of oxides.

Preference is given to the reducing agent used to carry out the reductive amination reaction of the compound of formula (VI) with the compound of formula (VII) being dihydrogen in the presence of palladium-on-carbon.

Preference is given to the reductive amination reaction of the compound of formula (VI) with the compound of formula (VII) being carried out at a dihydrogen pressure of from 0.5 to 1.5 bar.

Among the solvents which may be used to carry out the reductive amination reaction of the compound of formula (VI) with the compound of formula (VII) there may be mentioned, without implying any limitation, tetrahydrofuran, dichloromethane, 1,2-dichloroethane, acetates, alcohols, preferably ethanol, methanol or isopropanol, toluene and xylene.

Preference is given to the solvent used to carry out the reductive amination reaction of the compound of formula (VI) with the compound of formula (VII) comprising a mixture of ethanol and water.

The reductive amination reaction of the compound of formula (VI) with the compound of formula (VII) is preferably carried out at a temperature of from 0° C. to 40° C.

Among the organic solvents that may be used in the reaction between the compounds of formulae (VIII) and (IX) there may be mentioned, without implying any limitation, toluene, dichloromethane, 2-methyltetrahydrofuran, chlorobenzene, 1,2-dichloroethane, chloroform and dioxane.

Preference is given to the organic solvent used in the reaction between the compounds of formulae (VIII) and (IX) being dichloromethane.

The reaction between the compounds of formulae (VIII) and (IX) is preferably carried out at a temperature of from 0 to 40° C.

Among the bases that may be used in the reaction between the compounds of formulae (VIII) and (IX) there may be mentioned, without implying any limitation, pyridine, DMAP and tertiary amines, for example triethylamine, DIEA, N-methylpiperidine, DBU, DABCO, DBN and N-methylmorpholine.

Preference is given to the base used in the reaction between the compounds of formulae (VIII) and (IX) being triethylamine.

Among the acids that may be used to carry out cyclisation of the compound of formula (X) to form the compound of formula (V) there may be mentioned, without implying any limitation, concentrated sulphuric acid, polyphosphoric acid, concentrated hydrochloric acid in aqueous solution, concentrated hydrochloric acid in solution in acetic acid, concentrated hydrobromic acid in solution in acetic acid, and methanesulphonic acid.

Preference is given to the acid used to carry out cyclisation of the compound of formula (X) to form the compound of formula (V) being concentrated hydrochloric acid in solution in acetic acid.

The cyclisation reaction of the compound of formula (X) to form the compound of formula (V) in an acid medium is preferably carried out at a temperature of from 0 to 40° C.

The compounds of formulae (VIII) and (X) are new products which are useful as synthesis intermediates in the chemical or pharmaceutical industry, especially in the synthesis of ivabradine, addition salts thereof with a pharmaceutically acceptable acid and hydrates thereof, and as such they form an integral part of the present invention.

List of abbreviations used:
DABCO: 1,4-diazabicyclo[2.2.2]octane
DBN: 1,5-diazabicyclo[4.3.0]non-5-ene
DBU: 1,8-diazabicyclo[5.4.0]undec-7-ene
DIEA: N,N-diisopropylethylamine
DMAP: 4-dimethylaminopyridine
IR: infrared The Examples hereinbelow illustrate the invention.

The infrared spectra were recorded on a Bruker Tensor 27 infrared apparatus with a Golden Gate ATR accessory. The substances are placed on the plate in pure form.

EXAMPLE 1

2-{3-[{[(7S)-3,4-dimethoxybicyclo[4.2.0]octa-1,3,5-trien-7-yl]methyl}-(methyl)amino]propyl}-1H-isoindole-1,3(2H)-dione 5.3 g (25.5 mmoles) of 1-[(7S)-3,4-dimethoxybicyclo[4.2.0]octa-1,3,5-trien-7-yl]-N-methyl-methanamine and 6.8 g (25.5 mmoles) of 2-(3-bromopropyl)-1H-isoindole-1,3(2H)-dione are dissolved in 230 mL of acetone. 13 g (95 mmoles, 3.7 eq.) of potassium carbonate are added to the resulting solution. The mixture is then heated at reflux for 24 hours. After returning to ambient temperature, the potassium carbonate is filtered off and the filtrate is evaporated to dryness. The residue is taken up in water and extracted with dichloromethane. The organic phase is dried over $MgSO_4$, filtered and evaporated to dryness. 9.7 g of expected product are obtained in the form of a pale yellow oil.

Yield=97%

IR: $\nu$=2782, 1770, 1704, 1206, 836, 718 $cm^{-1}$.

EXAMPLE 2

N-{[(7S)-3,4-dimethoxybicyclo[4.2.0]octa-1,3,5-trien-7-yl]methyl}-N-methylpropane-1,3-diamine 9.7 g (24.58 mmoles) of the phthalimide compound from the previous Step are dissolved in 100 mL of ethanol. 2.7 mL (36.87 mmoles, 1.5 eq.) of hydrazine hydrate are added, and heating at reflux is carried out for 4 hours. After returning to ambient temperature, 100 mL of aqueous hydrochloric acid solution (4N) are added; the mixture is stirred for 1 hour at ambient temperature and filtered over a frit. The filtrate is then evaporated (removal of the ethanol). The aqueous phase is then washed twice with ether and brought to pH 9 by adding concentrated sodium hydroxide solution in the cold state. Extraction with dichloromethane is carried out 3 times and then the combined organic phases are washed with water, dried over $MgSO_4$, filtered and evaporated to dryness. 4.9 g of expected product are obtained in the form of a pale yellow oil.

Yield=75%

IR: $\nu$=3366, 3302, 1591 $cm^{-1}$.

EXAMPLE 3

N-{[(7S)-3,4-dimethoxybicyclo[4.2.0]octa-1,3,5-trien-7-yl]methyl}-N'-(2,2-dimethoxyethyl)-N-methylpropane-1,3-diamine 1 g (3.7 mmoles) of N-{[(7S)-3,4-dimethoxybicyclo[4.2.0]octa-1,3,5-trien-7-yl]methyl}-N-methylpropane-1,3-diamine is dissolved in 20 mL of ethanol. 520 mg (0.45 mL) of a 60% solution of glyoxal 1,1-dimethyl acetal in water and then 100 mg of Pd/C 10% are added. The reaction mixture is hydrogenated at atmospheric pressure and ambient temperature for 12 hours. The catalyst is filtered off and the filtrate is evaporated to dryness. 1.2 g of expected product are obtained in the form of an oil.

Yield=90%

IR: $\nu$=1207, 1508, 834 $cm^{-1}$.

EXAMPLE 4

N-{3-[{[(7S)-3,4-dimethoxybicyclo[4.2.0]octa-1,3,5-trien-7-yl]methyl}-(methyl)amino]propyl}-N-(2,2-dimethoxyethyl)-2-(3,4-dimethoxyphenyl)acetamide A solution of 6.3 g (17.9 mmoles) of the acetal from the previous Step in 80 mL of $CH_2Cl_2$ is prepared. 5 mL of triethylamine (35.8 mmoles, 2 eq.) are added to the resulting solution, which is then cooled to 0° C. A solution of 3.8 g (17.9 mmoles) of homoveratryl chloride in 40 mL of dichloromethane is then added thereto dropwise. Stirring is then carried out for 3 hours at ambient temperature. The mixture is diluted with water and extracted with dichloromethane. The organic phase is dried over $MgSO_4$, filtered and evaporated to dryness. There are obtained 10 g of an oil which is purified on 500 g of silica gel (eluant =$CH_2Cl_2$/EtOH: 90/10). 8.5 g of expected product are obtained in the form of a brown oil.

Yield=90%

IR: $\nu$=1627, 1207, 1124, 1071, 1049, 1027 $cm^{-1}$.

EXAMPLE 5

3-{3-[{[(7S)-3,4-dimethoxybicyclo[4.2.0]octa-1,3,5-trien-7-yl]-methyl}-(methyl)amino]propyl}-7,8-dimethoxy-1,3-dihydro-2H-3-benzazepin-2-one To a mixture of 10 mL of acetic acid and 10 mL of concentrated hydrochloric acid there is added 1 g (1.9 mmoles) of the acetal from the previous Step at ambient temperature. Stirring is carried out at 25° C. for 1 hour. The solution is brought to pH 9 by adding ice and aqueous sodium hydroxide solution (20%). The mixture is then extracted with dichloromethane. The organic phase is washed with water, dried over $MgSO_4$, filtered and evaporated to dryness. There is obtained 1 g of an oil which is purified by flash chromatography on 40 g of silica (Merck™ column, eluant =$CH_2Cl_2$/EtOH: 95/5). There are obtained 270 mg of expected product in the form of an oil having an optical purity of more than 99%.

Yield=31%

IR: $\nu$=1656, 836, 760 $cm^{-1}$.

EXAMPLE 6

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one The title compound is obtained by reproducing Step D of Example 1 of patent specification EP 0 534 859 starting from the compound of Example 5 hereinbefore.

The invention claimed is:

1. A process for the synthesis of ivabradine of formula (I):

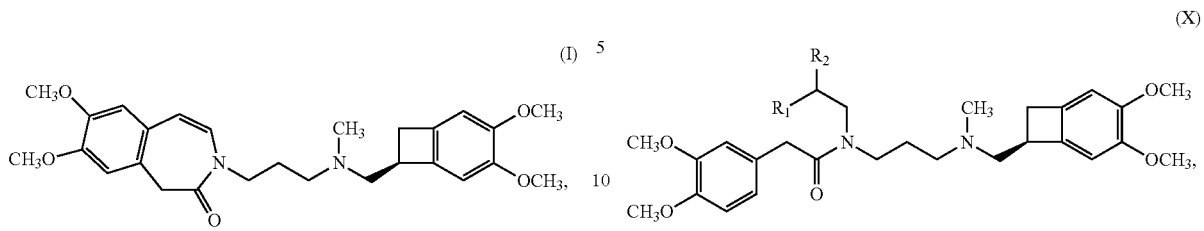

(I)

wherein a compound of formula (VI):

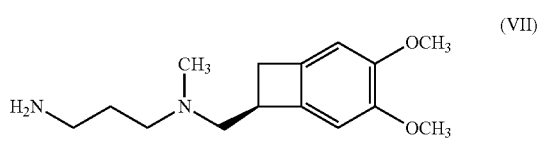

(VI)

wherein $R_1$ and $R_2$, which are the same or different, represent linear or branched $(C_1-C_6)$alkoxy groups or together with the carbon atom carrying them form a 1,3-dioxane, 1,3-dioxolane or 1,3-dioxepane ring, is subjected to a reductive amination reaction with a compound of formula (VII):

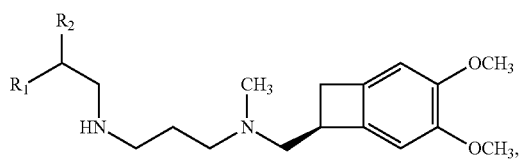

(VII)

in the presence of a reducing agent, in an organic solvent, a mixture of organic solvents or a mixture of organic solvent(s) and water, to yield a compound of formula (VIII):

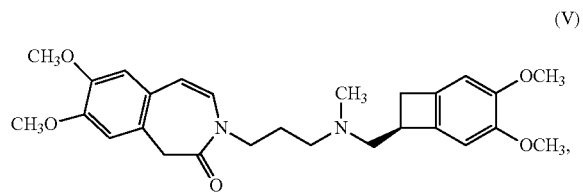

(VIII)

wherein $R_1$ and $R_2$ are as defined hereinbefore, which is subjected to a condensation reaction with a compound of formula (IX):

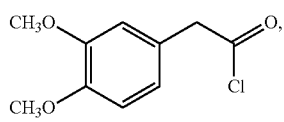

(IX)

in the presence of a base in an organic solvent, to yield a compound of formula (X):

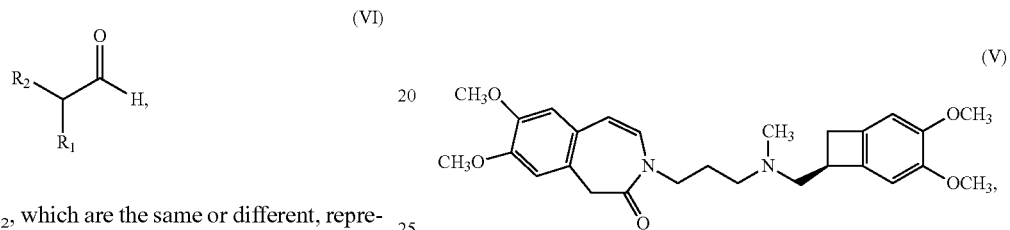

(X)

wherein $R_1$ and $R_2$ are as defined hereinbefore, which is subjected to a cyclisation reaction in an acid medium to yield a compound of formula (V):

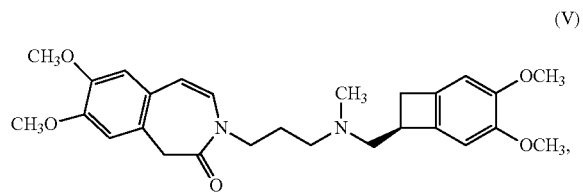

(V)

which is subjected to a hydrogenation reaction to yield ivabradine of formula (I), which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

2. The process according to claim 1, wherein the reducing agent used to carry out the reductive amination reaction of the compound of formula (VI) with the compound of formula (VII) is selected from sodium triacetoxyborohydride, sodium cyanoborohydride, and dihydrogen in the presence of a catalyst.

3. The process according to claim 2, wherein the catalyst is selected from palladium, platinum, nickel, ruthenium, rhodium, and compounds thereof, optionally on a support or in the form of oxides.

4. The process according to claim 2, wherein the reducing agent used to carry out the reductive amination reaction of the compound of formula (VI) with the compound of formula (VII) is dihydrogen in the presence of palladium-on-carbon.

5. The process according to claim 4, wherein the reductive amination reaction between the compound of formula (VI) and the compound of formula (VII) is carried out at a dihydrogen pressure of from 0.5 to 1.5 bar.

6. The process according to claim 1, wherein the solvent used to carry out the reductive amination reaction of the compound of formula (VI) with the compound of formula (VII) is selected from tetrahydrofuran, dichloromethane, 1,2-dichloroethane, acetates and alcohols, toluene and xylene.

7. The process according to claim 6, wherein the solvent used to carry out the reductive amination reaction of the compound of formula (VI) with the compound of formula (VII) is selected from ethanol, methanol and isopropanol.

8. The process according to claim 6, wherein the solvent used to carry out the reductive amination reaction of the compound of formula (VI) with the compound of formula (VII) comprises a mixture of ethanol and water.

9. The process according to claim 1, wherein the reductive amination reaction between the compound of formula (VI) and the compound of formula (VII) is carried out at a temperature of from 0 to 40° C.

10. The process according to claim 1, wherein the organic solvent used in the reaction between the compounds of formulae (VIII) and (IX) is selected from toluene, dichloromethane, 2-methyltetrahydrofuran, chlorobenzene, 1,2-dichloroethane, chloroform and dioxane.

11. The process according to claim 10, wherein the organic solvent used in the reaction between the compounds of formulae (VIII) and (IX) is dichloromethane.

12. The process according to claim 1, wherein the reaction between the compounds of formulae (VIII) and (IX) is carried out at a temperature of from 0 to 40° C.

13. The process according to claim 1, wherein the base used in the reaction between the compounds of formulae (VIII) and (IX) is selected from pyridine, 4-dimethylaminopyridine (DMAP) and a tertiary amine.

14. The process according to claim 13, wherein the base used in the reaction between the compounds of formulae (VIII) and (IX) is triethylamine.

15. The process according to claim 1, wherein the acid used to carry out cyclisation of the compound of formula (X) to form the compound of formula (V) is selected from concentrated sulphuric acid, polyphosphoric acid, concentrated hydrochloric acid in aqueous solution, concentrated hydrochloric acid in solution in acetic acid, concentrated hydrobromic acid in solution in acetic acid, and methanesulphonic acid.

16. The process according to claim 15, wherein the acid used to carry out cyclisation of the compound of formula (X) to form the compound of formula (V) is concentrated hydrochloric acid in solution in acetic acid.

17. The process according to claim 1, wherein cyclisation of the compound of formula (X) to form the compound of formula (V) is carried out at a temperature of from 0 to 40° C.

18. A compound selected from those of formula (VIII):

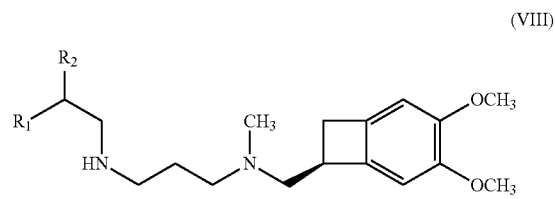

(VIII)

wherein $R_1$ and $R_2$, which are the same or different, represent linear or branched $(C_1$-$C_6)$alkoxy groups or together with the carbon atom carrying them form a 1,3-dioxane, 1,3-dioxolane or 1,3-dioxepane ring.

19. A compound selected from those of formula (X):

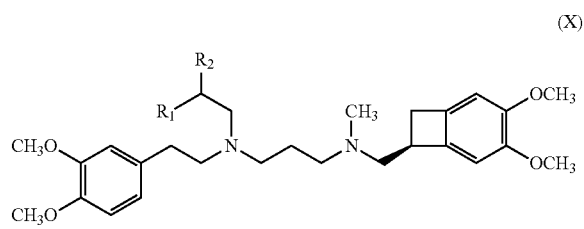

(X)

wherein $R_1$ and $R_2$ which are the same or different, represent linear or branched $(C_1$-$C_6)$alkoxy groups or together with the carbon atom carrying them form a 1,3-dioxane, 1,3-dioxolane or 1,3-dioxepane ring.

* * * * *

UNITED STATES PATENT AND TRADEMARK OFFICE
CERTIFICATE OF CORRECTION

PATENT NO. : 8,476,426 B2  
APPLICATION NO. : 13/369690  
DATED : July 2, 2013  
INVENTOR(S) : Jean-Louis Peglion and Aimee Dessinges Page 1 of 1

It is certified that error appears in the above-identified patent and that said Letters Patent is hereby corrected as shown below:

In the Claims

Column 7, Line 5, Claim 1:

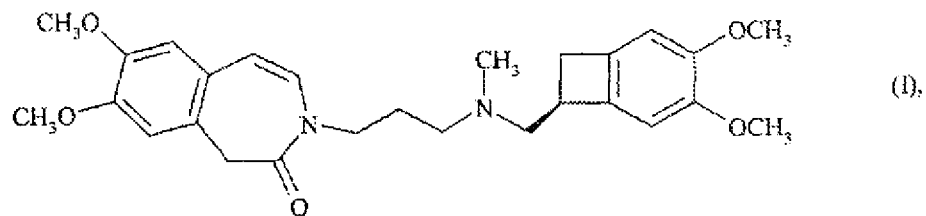

Should be

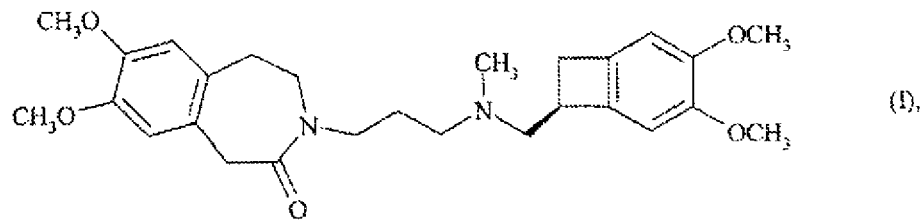

Signed and Sealed this  
Thirteenth Day of August, 2013

Teresa Stanek Rea  
*Acting Director of the United States Patent and Trademark Office*